US010541756B2

(12) United States Patent
Hendrickson et al.

(10) Patent No.: US 10,541,756 B2
(45) Date of Patent: Jan. 21, 2020

(54) WAVEFRONT SHAPING WITH COHERENT OPTICAL SENSING

(71) Applicant: The Johns Hopkins University, Baltimore, MD (US)

(72) Inventors: Scott M. Hendrickson, Baltimore, MD (US); David W. Blodgett, Ellicott City, MD (US); Clare W. Lau, Kensington, MD (US); Jeremiah J. Wathen, Annapolis, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 16/210,183

(22) Filed: Dec. 5, 2018

(65) Prior Publication Data

US 2019/0173587 A1    Jun. 6, 2019

Related U.S. Application Data

(60) Provisional application No. 62/594,739, filed on Dec. 5, 2017.

(51) Int. Cl.
| | |
|---|---|
| *H04B 10/50* | (2013.01) |
| *H04B 10/63* | (2013.01) |
| *H04B 10/64* | (2013.01) |
| *H04B 10/61* | (2013.01) |
| *H04B 10/67* | (2013.01) |
| *H04B 13/00* | (2006.01) |
| *A61B 5/00* | (2006.01) |
| *G02B 27/00* | (2006.01) |
| *G01N 21/49* | (2006.01) |
| *G01J 9/02* | (2006.01) |

(52) U.S. Cl.
CPC ......... *H04B 10/614* (2013.01); *A61B 5/0066* (2013.01); *G01J 9/02* (2013.01); *G01N 21/49* (2013.01); *G02B 27/0025* (2013.01); *H04B 10/6161* (2013.01); *H04B 10/6165* (2013.01); *H04B 10/676* (2013.01); *H04B 13/005* (2013.01); *G01J 2009/0211* (2013.01)

(58) Field of Classification Search
CPC combination set(s) only.
See application file for complete search history.

(56) References Cited

U.S. PATENT DOCUMENTS

2012/0197133 A1* 8/2012 McKenna ............ A61B 5/0075
                                                              600/476
2017/0187442 A1* 6/2017 Luddy .................... H04J 11/00

* cited by examiner

*Primary Examiner* — Shi K Li
(74) *Attorney, Agent, or Firm* — Sung T. Kim (57) ABSTRACT

An example imaging system may include a spatial light modulator and a coherent optical receiver. The spatial light modulator may be configured to receive an optical input wave and perform wavefront shaping on the optical input wave to output a shaped wave. The coherent optical receiver may include an optical local oscillator, an optical beam splitter, an optical detector, and processing circuitry. The optical detector may be configured to receive a mixed wave from the optical beam splitter that is based on the mixing of a local oscillator wave with a scattering medium output wave that at least initially comprises a speckle pattern formed by the shaped wave interacting with a scattering medium. The processing circuitry may be configured to perform coherent detection on the mixed wave to extract optical amplitude and phase information, and provide an error signal as feedback to the spatial light modulator for performing iterative wavefront shaping.

20 Claims, 5 Drawing Sheets

WAVEFRONT SHAPING WITH COHERENT OPTICAL SENSING

CROSS-REFERENCE TO RELATED APPLICATIONS

This application claims the benefit of U.S. Provisional Application No. 62/594,739 filed on Dec. 5, 2017, the entire contents of which are hereby incorporated herein by reference.

TECHNICAL FIELD

Exemplary embodiments of the present disclosure generally relate to optical imaging techniques, and more specifically relate to optical imaging correction techniques that are applicable to light wave interaction with a scattering medium.

BACKGROUND

Light waves are refracted or reflected as they pass through or are reflected from a scattering medium. Correcting for these changes to the light would allow for the re-creation of the light as it was prior to entering the scattering medium. A highly-scattering medium is one where received light scatters many times within the medium before being transmitted or reflected out of the medium. Such scattering media are present in a vast number of applications. The applications can range from the scattering effects of the Earth's atmosphere on light received from distant stars to the scattering effects of the skin and soft tissue when using light to image bones and organs internal to the body.

When light is highly scattered by such a medium, speckle patterns of light can be formed at a receiving device or a receiving surface. These speckle patterns maintain useful information about the light prior to interacting with the scattering medium. The maintained information in the speckle patterns may be correlated to specific characteristics of the light entering the scattering medium, and therefore can be leveraged to account and correct for the scattering that is introduced by the scattering medium. While these characteristic correlations between the light prior to and after interaction with the scattering medium have proven to be useful to some degree, there continues to be difficulty when addressing the effects that arise from light wave interactions with highly-scattering media. As such, the effects of a highly-scattering medium on an imaging system continues to pose a technical problem for resolving the aberrations and other effects that highly-scattering media cause to received light.

BRIEF SUMMARY OF SOME EXAMPLES

According to some example embodiments, an imaging system is provided. The imaging system may comprise a spatial light modulator and a coherent optical receiver. The spatial light modulator may be configured to receive an optical input wave and perform wavefront shaping on the optical input wave to output a shaped wave. The coherent optical receiver may comprise an optical local oscillator, an optical beam splitter, an optical detector, and processing circuitry. The optical local oscillator may be configured to output a local oscillator wave at a local oscillator frequency. The optical beam splitter may be configured to receive a scattering medium output wave and the local oscillator wave and mix the scattering medium output wave with the local oscillator wave to form a mixed wave. In this regard, the scattering medium output wave may be a resultant wave of the shaped wave interacting with a scattering medium and the scattering medium output wave may at least initially comprise a speckle pattern. The optical detector may be configured to receive the mixed wave and output an electrical signal representative of the mixed wave. The processing circuitry may be configured to receive the electrical signal from the optical detector, perform coherent detection on the electrical signal to extract optical amplitude and phase information corresponding to the mixed wave, and provide an error signal as feedback to the spatial light modulator for performing iterative wavefront shaping of the optical input wave. The error signal may indicate the optical amplitude and phase information.

According to some example embodiments, a method is provided. The method may comprise receiving an optical input wave at a spatial light modulator, and performing wavefront shaping, by the spatial light modulator, on the optical input wave to form a shaped wave. The method may also comprise causing the shaped wave to interact with a scattering medium to form a scattering medium output wave at least initially comprising a speckle pattern, mixing the scattering medium output wave with a local oscillator wave to form a mixed wave, and receiving the mixed wave at an optical detector. Further, the method may comprise performing coherent detection on the mixed wave to extract optical amplitude and phase information, and providing an error signal as feedback to the spatial light modulator for performing iterative wavefront shaping on the optical input wave, the error signal indicating the optical amplitude and phase information.

An apparatus in the form of a coherent optical receiver is provided. The apparatus may comprise an optical local oscillator, an optical beam splitter, an optical detector, and processing circuitry. The optical local oscillator may be configured to output a local oscillator wave at a local oscillator frequency. The optical beam splitter may be configured to receive a scattering medium output wave and the local oscillator wave and mix the scattering medium output wave with the local oscillator wave to form a mixed wave. In this regard, the scattering medium output wave may at least initially comprise a speckle pattern and the scattering medium output wave may be a resultant wave of a shaped wave, subjected to wavefront shaping, interacting with a scattering medium. The optical detector may be configured to receive the mixed wave and output an electrical signal representative of the mixed wave. The processing circuitry may be configured to receive the electrical signal from the optical detector, perform coherent detection on the electrical signal to extract optical amplitude and phase information, and provide an error signal as feedback to the spatial light modulator for performing iterative wavefront shaping of the optical input wave. The error signal may indicate the optical amplitude and phase information.

BRIEF DESCRIPTION OF THE SEVERAL VIEWS OF THE DRAWING(S)

Having thus described some embodiments in general terms, reference will now be made to the accompanying drawings, which are not necessarily drawn to scale, and wherein:

DETAILED DESCRIPTION

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout.

According to various example embodiments, systems, apparatuses, and methods are provided to correct for the scattering effects of a highly-scattering medium (also referred to as a "scattering medium" herein) on a light wave that may be used for imaging. In this regard, according to some example embodiments, a spatial light modulator may be employed that performs wavefront shaping of an optical input wave based on an error signal received in the form of feedback received from a coherent optical receiver. The spatial light modulator may perform, according to some example embodiments, an iterative wavefront shaping process to adjust the phase and amplitude of an optical input wave to form a shaped wave to pass through the scattering medium. The iterative process may be based, in part, upon a speckle pattern that is formed by the shaped wave interacting with the scattering medium.

However, since a coherent optical receiver is being utilized, the wave leaving the scattering medium may also be mixed, via a beam splitter, with a local oscillator wave. The local oscillator wave may be chosen or determined, for example, based on a frequency of the optical input wave, to cause heterodyne or homodyne mixing. The resulting mixed wave may include a coherent gain that can facilitate wave analysis in the form of coherent detection. The mixed wave may, therefore, be received by an optical detector, which may be operably coupled to processing circuitry. The processing circuitry may be configured to analyze the signals from the optical detector to perform coherent detection. Since the speckle pattern exhibits certain correlations (e.g., certain attributes or patterns remain fixed over certain time intervals), these may be leveraged by the processing circuitry to analyze the received speckle pattern and output a feedback signal to the spatial light modulator that includes both phase and amplitude information. Based on iterations of the system and the feedback signal, the spatial light modulator may make respective iterative adjustments to the wavefront shaping of the optical input wave. The adjustments resulting in the shaped wave may ultimately cause the wave being received by the optical detector to be focused at a selected location on the detector, for example, on a single pixel of the detector. When the intensity of the wave received at the optical detector, for example at the selected location on the detector, is greater than a threshold intensity or has increased by a threshold intensity from an initial intensity, then the wavefront shaping may be considered optimized. Once optimized, the resulting focused wave received by the optical detector may be further analyzed to extract information for imaging purposes.

The structures and techniques described herein may be applicable in a variety of settings. Some examples of imaging applications that may benefit from the example embodiments described herein include coherent LIDAR (light detection and ranging), free-space coherent optical communications, coherent speckle correlation imaging, optical vibrometry, and the like.

Figure 1:
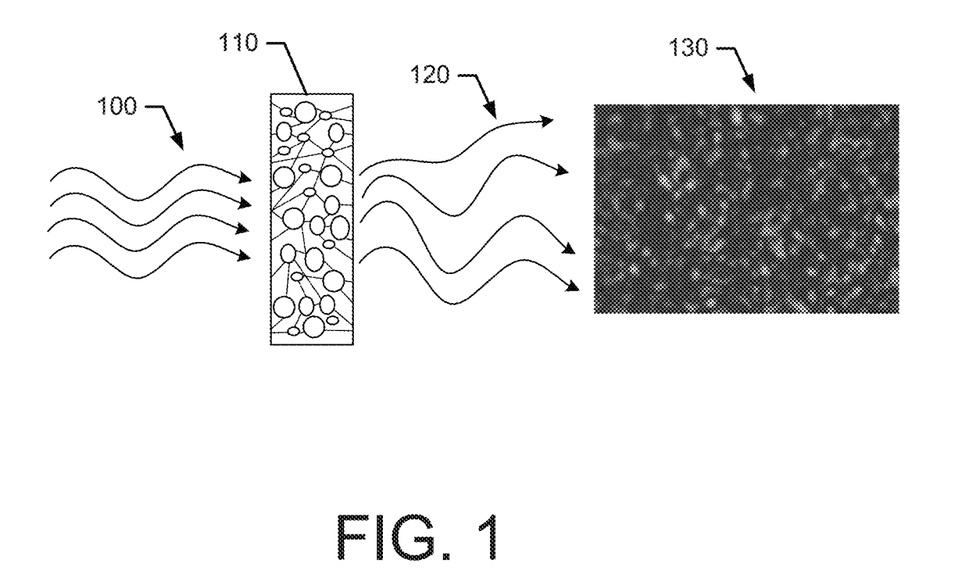
FIG. 1 is an illustration of an optical wave passing through a scattering medium.

In light of the forgoing, FIG. 1 provides an illustration of an optical input wave 100 passing through a scattering medium 110. The optical input wave 100 may be provided from a variety of sources for the purpose of, for example, performing optical imaging. Example sources may include light from a star, a light wave from a laser (e.g., single frequency laser) or other light generating device that may be used to illuminate through a scattering medium, such as biological tissue, to illuminate, for example, internal features to a body such as organs, muscles, tendons, ligaments, or the like. The optical input wave 100 may be directed to interact with the scattering medium 110. The scattering medium 110 may be an object that causes multiple internal scattering events in the form of reflections or refractions within the object as the optical input wave 100 passes through the scattering medium 110. Examples of a such a scattering medium 110 may also include biological tissues, bone, turbid water, or the like.

As the optical input wave 100 exits the scattering medium 110, a scattered wave 120 is formed. Due to the scattering events within the scattering medium 110, the scattered wave 120 may be split into multiple paths or modes of light. If the scattered wave 120 interacts with, for example, a planar surface, the scattered wave 120 can create a speckle pattern 130 on the planar surface. The speckle pattern 130 may be caused by the multiple modes of light of the scattered wave 120 interfering with each other constructively and destructively.

Despite appearing to be quite random, the resulting speckle pattern 130 nonetheless includes valuable properties that can be exploited in order to concentrate light within the scattering media 110 or to mitigate its effects and image through the scattering media 110. In this regard, the speckle pattern 130 retains correlations in time, space, and optical frequency, or stated differently, the speckle pattern, or aspects of the speckle pattern, remains stationary over certain time, length and optical wavelength variations which allows sufficient time for a wavefront optimization algorithm to converge. As such, according to some example embodiments, speckle correlations in time, space and frequency may be leveraged in order to optimize some aspect of the optical propagation of the system (e.g., localization within the scattering medium or focusing onto a detector after propagation through scattering media).

Figure 2:
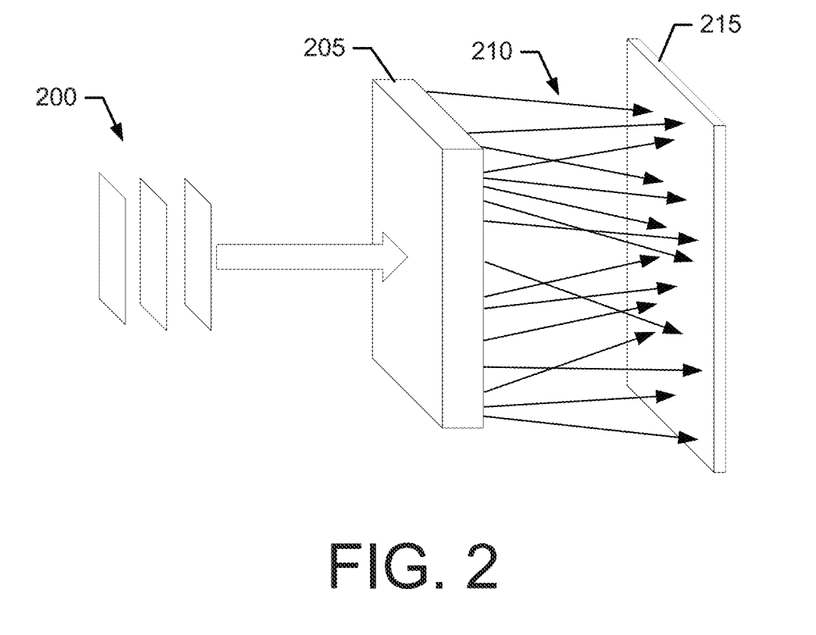
FIG. 2 is another illustration of an optical wave passing through a scattering medium.

Similar to FIG. 1, FIG. 2 provides another illustration of an optical wave passing through a scattering medium. In this regard, the optical input wave 200 is shown as propagating through a scattering medium 205. The scattering medium 205 may be the same or similar to the scattering medium 110, described above with respect to FIG. 1. As shown in FIG. 2, when the optical input wave 200 exits the scattering medium 205, multiple interfering paths of light 210 are formed that are received by the planar surface 215. Due to interference between the paths of light 210, a speckle pattern may be formed on the planar surface 215. In some embodiments, information extracted from the speckle pattern may be used to shape the optical input wave 200. The shaped optical input wave 200 may be propagated through the scattering medium 205, forming a new (but more focused) speckle pattern on the planar surface, from which information may again be extracted to further shape the optical input wave 200. This process may be repeated until an optimized wavefront shaping is achieved for the optical input wave 200.

Figure 3:
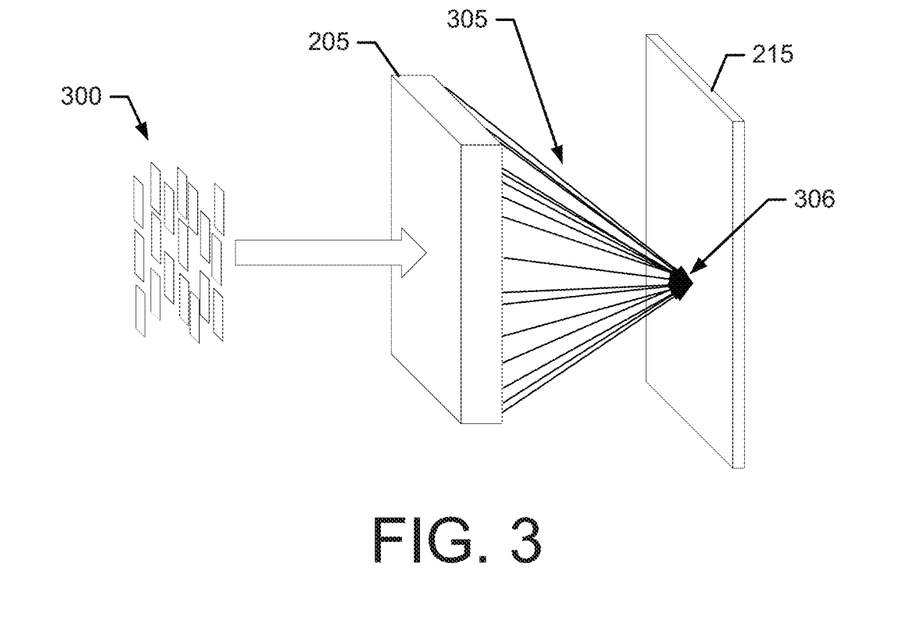
FIG. 3 is an illustration of a shaped wave formed via a wavefront shaping process according to some example embodiments passing through a scattering medium.

FIG. 3 is an illustration of the application of a shaped wave 300 to the scattering medium 205. In this regard, the shaped wave 300 may have been iteratively formed, as described above, to achieve an optimized wavefront shaping. In this regard, the shaped wave 300 may be formed by, for example, a spatial light modulator configured to perform wavefront shaping. FIG. 3 illustrates a scenario where, according to some example embodiments, the wavefront shaping process has already occurred, resulting in the shaped wave 300 that has been optimized for the scattering medium 205. Accordingly, as the shaped wave 300 passes through the scattering medium 205, the light 305 exiting the scattering medium 205 is focused at a selected location 306 on the planar surface 215 and may be referred to as focused wave due to, for example, an optimization process. According to some example embodiments, the wavefront shaping resulting in shaped wave 300 may cause light 305 to be focused onto, for example, a single pixel of an optical detector on the planar surface 215.

Figure 4:
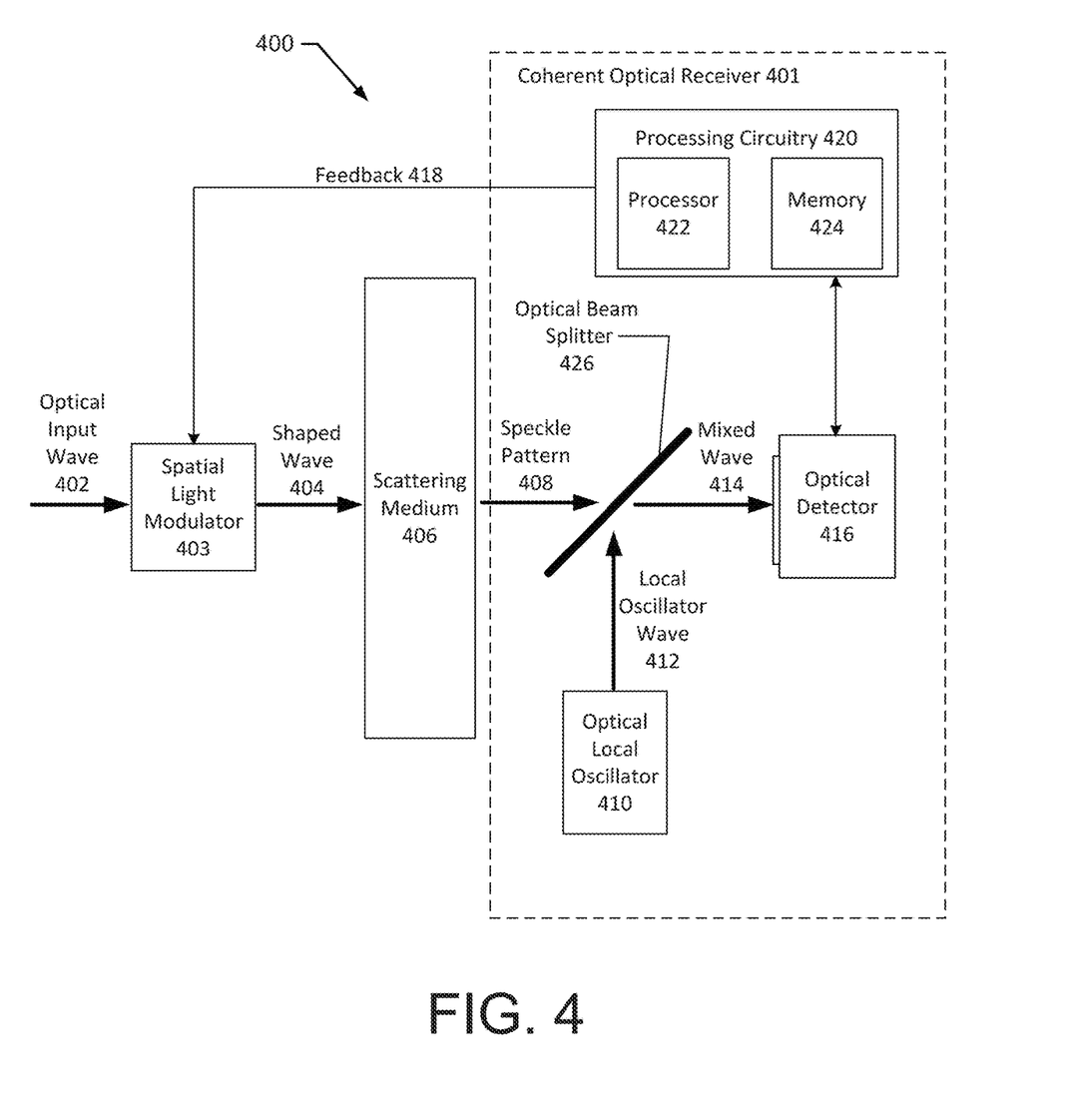
FIG. 4 illustrates a block diagram of an imaging system comprising a coherent optical receiver and a scattering medium in a transmission configuration according to various example embodiments.

FIG. 4 illustrates a block diagram of imaging system 400, according to some example embodiments, configured to operate in a transmission configuration relative to the scattering medium 406 (i.e., the optical input wave passes through the scattering medium to be received on an opposite side of the scattering medium). The system 400 may comprise a coherent optical receiver 401 according to various example embodiments. The system 400 may also include a spatial light modulator 403. According to some example embodiments, as further described herein, via the spatial light modulator 403, an optical input wave 402 may be subjected to an iterative wavefront shaping process based on, for example, closed-loop feedback provided by the coherent optical receiver 401.

The coherent optical receiver 401 may comprise an optical beam splitter 426, an optical local oscillator 410, an optical detector 416, and processing circuitry 420. According to some example embodiments, the optical beam splitter 426 and the optical local oscillator 410 may be external to, for example, a housing of the optical detector 416 but the optical beam splitter 426 and the optical local oscillator 410 may still be operably coupled to the optical detector 416 to operate as otherwise described herein. The optical beam splitter 426 may be configured to mix two input waves to provide an output mixed wave. As described in further detail below, the optical beam splitter 426 may be configured to mix an input wave with a local oscillator wave 412 provided by the optical local oscillator 410. According to some example embodiments, the optical beam splitter 426 may be a two triangular glass prisms affixed together with a resin. According to some example embodiments, the optical beam splitter 426 may be a half-silvered mirror with a transparently thin coating of metal (e.g., aluminum) or a dichroic optical coating.

The optical local oscillator 410 may be embodied in a number of forms. With respect to operation, according to some example embodiments, the optical local oscillator 410 may be configured to output a local oscillator wave 412 for mixing via the optical beam splitter 426 of the coherent optical receiver 401. To do so, the optical local oscillator 410 may be embodied as, for example, a laser diode or other light generating device that may, according to some example embodiments, have a controllable frequency. According to some example embodiments, the local oscillator wave 412 may be generated from or picked-off from the optical input wave 402 and may have a frequency that is the same as a frequency of the optical input wave 402. In this regard, the optical input wave 402 may be split using a beam splitter to form a second path for the optical input wave 402. The optical input wave 402 traveling the second path may, in some example embodiments be filtered, and subsequently used as the local oscillator wave 412.

The optical detector 416 of the coherent optical receiver 401 may be configured to receive an optical wave and convert the received optical wave into electrical signals that may be processed. In this regard, the optical detector 416 may be a form of optical sensor. In some example embodiments, the optical detector 416 may be a camera-type sensor that is pixelated or monolithic.

The optical detector 416 may be operably coupled to processing circuitry 420. The processing circuitry 420 may be configurable to perform operations in accordance with example embodiments described herein. As such, for example, at least some of the functions attributable to the coherent optical receiver 401 may be carried out by or otherwise instructed by the processing circuitry 420. In some example embodiments, the processing circuitry 420 may be embodied as a chip or chip set. In other words, the processing circuitry 420 may comprise one or more physical packages (e.g., chips) including materials, components and/or wires on a structural assembly (e.g., a baseboard). In an example embodiment, the processing circuitry 420 may include one or more instances of a processor 422 and memory 424. As such, the processing circuitry 420 may be embodied as one or more instances of a circuit chip (e.g., an integrated circuit chip) configured (e.g., with hardware, software or a combination of hardware and software) to perform operations described herein.

In some example embodiments, the memory 424 may include one or more non-transitory memory devices such as, for example, volatile and/or non-volatile memory that may be either fixed or removable. The memory 424 may be configured to store information, data, applications, instructions or the like for enabling the coherent optical receiver 401 to carry out various functions in accordance with example embodiments of the present invention. For example, the memory 424 could be configured to buffer input data for processing by the processor 422. Additionally or alternatively, the memory 424 may be configured to store instructions for execution by the processor 422.

The processor 422 may be embodied in a number of different ways. For example, the processor 422 may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. In an example embodiment, the processor 422 may be configured to execute instructions stored in the memory 424 or otherwise accessible to the processor 422. As such, whether configured by hardware or by a combination of hardware and software, the processor 422 may represent an entity (e.g., physically embodied in circuitry—in the form of processing circuitry 420) capable of performing operations according to embodiments of the present invention while configured accordingly. Thus, for example, when the processor 422 is embodied as an ASIC, FPGA or the like, the processor 422 may be specifically configured hardware for conducting the operations described herein. Alternatively, as another example, when the processor 422 is embodied as an executor of software instructions, the instructions may specifically configure the processor 422 to perform the operations described herein.

In an example embodiment, the processor 422 (or the processing circuitry 420) maybe embodied as, include or otherwise control the coherent optical receiver 401. As such, in some embodiments, the processor 422 (or the processing circuitry 420) may be said to cause each of the operations described in connection with the coherent optical receiver 401 to undertake the corresponding functionalities responsive to execution of instructions or algorithms configuring the processor 422 (or processing circuitry 420) accordingly.

Having described some structural aspects of the components of the imaging system 400, the following provides further details on the operation and configuration of the imaging system 400 and, more specifically, the coherent optical receiver 401. In this regard, the imaging system 400 may receive an optical input wave 402. The optical input wave 402 may be provided by a variety of sources depending on the type of application for the imaging system 400. Example sources may include a light wave from a laser or other light generating device that may be used to illuminate through a scattering medium, such as biological tissue to illuminate internal features to a body such as organs, muscles, tendons, ligaments, or the like. The optical input wave 402 may include information for extraction via imaging. However, due to the presence of the scattering medium 406, the information may be difficult to extract directly from the optical input wave 402 after having passed through the scattering medium 406.

In this regard, the optical input wave 402 may be received by the spatial light modulator 403. According to some example embodiments, the spatial light modulator 403 may comprise a two-dimensional grid of nematic liquid crystals elements or pixels, which may be configured to alter an optical phase of received light. According to some example embodiments, the spatial light modulator 403 may be configured to alter an optical phase of received light but not an amplitude of the received light. The spatial light modulator 403 may be configured to perform wavefront shaping by controlling a grid of pixels. In this regard, for example, each pixel may be controlled to impart a different optical delay (i.e., phase) such that an error signal received from the coherent optical receiver 401 as feedback 418 can be optimized on the coherent receiver. According to some example embodiments, the error signal may include at least phase information that can be correlated to input paths or modes of light within the optical input wave 402 and can be gathered from a speckle pattern formed by the optical input wave 402 interacting with the scattering medium 406. As the optical input wave 402 interacts with the spatial light modulator 403, each component path of the optical input wave 402 may interact with a respective pixel of the spatial light modulator 403. As such, by controlling the pixels of the spatial light modulator 403 the component paths of the optical input wave 402 may be altered by, for example, introducing an optical delay or phase based on the feedback 418 from the coherent optical receiver 401. For example, an optical phase between 0 and 2 pi of each pixel of the spatial light modulator 403 may be introduced. According to some example embodiments, since amplitude information is also provided in error signal, the pixels of the spatial light modulator 403 may also be controlled based on the amplitude information that may be correlated to component modes or paths of the optical input wave 402. With the component paths altered in this manner, a new shaped wave 404 may be output from the spatial light modulator 403. The shaped wave 404 may therefore have component paths that interact differently with the scattering medium 406, which may lead to, for example, lesser instances of scattering as the shaped wave 404 interacts with the scattering medium. As further described herein, by leveraging the error signal provided as feedback 418, iterative changes can be made to the optical delay or phase changes introduced by each pixel of the spatial light modulator 403 to ultimately cause an optimized shaped wave 404 to be output from the spatial light modulator 403.

Thus, the error signal generated by the coherent optical receiver 401 may be computed from both the amplitude and phase of the mixed wave 414 (i.e., coherent signal) received by the optical detector 416. For example, the error signal may include quantities, such as the magnitude of the light in a given region of interest or a phase relationship between light received at different parts of an array of the optical detector. As such, based on the error signal, the shaped wave 404 may be formed and provided to and propagate into the scattering medium 406, which may be similar to scattering medium 110 or 205.

The output from the scattering medium 406 may be referred to as the scattering medium output wave 408. As further describe herein, the scattering medium output wave 408 may initially comprise a speckle pattern, but after a series of wavefront shaping iterations, the scattering medium output wave 408 may be a focused wave. The scattering medium output wave 408 may be received as an input to the coherent optical receiver 401. Further, the scattering medium output wave 408 may be mixed with a local oscillator wave 412, via an optical beam splitter 426, to output a mixed wave 414. The mixing of the scattering medium output wave 408 with the local oscillator wave 412 can operate to support coherent detection by the processing circuitry 420 by introducing a coherent gain to the mixed wave 414. By increasing the coherent gain in this manner, noise in the form of shot noise dominates relative to noise introduced by, for example, the optical detector 416, thereby recognizing an improvement in signal to noise. According to some example embodiments, the mixing performed at the optical beam splitter 426 may be heterodyne or homodyne mixing with the scattering medium output wave 408 based on the frequency of the local oscillator wave 412.

According to some example embodiments, the mixed wave 414 may be received by the optical detector 416. Prior to optimization of the shaped wave 404 via the iterative process, the mixed wave 414 may be received at the optical detector 416 in the form of a speckle pattern. In this regard, the optical detector 416 may be configured to convert the received mixed wave 414 (e.g., speckle pattern for a non-optimized mixed wave 414) into electrical signals for delivery to the processing circuitry 420. The processing circuitry 420 may be configured to perform coherent detection on the electrical signals. In this regard, to perform coherent detection, the processing circuitry 420 may be configured to demodulate the received signals and compute variables (e.g., decision variables) based on the electrical signals representative of the mixed wave 414 that contain both amplitude and phase information. According to some example embodiments, frequency information may also be determined. One or more of the amplitude, phase, and frequency information may be provided to the spatial light modulator 403 as feedback 418 in the form of an error signal.

As indicated above, the spatial light modulator 403 may be configured to perform an iterative process of wavefront shaping of the optical input wave 402 based on the error signal that is provided as feedback 418. During an initial iteration, according to some example embodiments, the spatial light modulator 403 may make no change to the received optical input wave 402 since the spatial light modulator 403 has not yet received a first error signal as feedback 418. Subsequently, the amplitude and phase information determined via the coherent detection and included in the error signal may be used to iteratively adjust the optical input wave 402 to generate a more optimized shaped wave 404, until the shaped wave 404 is considered optimized. Initially, the scattering medium output wave 408 may include a speckle pattern that may be poorly focused. However, through an iterative wavefront shaping process, the spatial light modulator 403 may be configured to improve the shaped wave 404 that is provided to the scattering medium 406 and cause the speckle pattern of the scattering medium output wave 408 to become a focused wave.

In this regard, wavefront shaping, according to some example embodiments, can be based on the principle that scattering caused by the scattering medium 406 can act to randomize input modes or paths of light as described above with respect to FIGS. 1 and 2. However, the effect of the wavefront shaping process can map each input mode of the optical input wave 402 to all output modes leaving the scattering medium 406. Accordingly, since the spatial light modulator 403 is positioned upstream of the scattering medium 406, the spatial light modulator 403 can perform phase control on each input mode to the scattering medium 406 to redirect the power on the output wave from the scattering medium 406 using optical interference. To do so, the iterative wavefront shaping process may be performed based on an iterative algorithm. Examples of some algorithms that may be used include gradient ascent algorithms and genetic algorithms. These algorithms can either use the coherent magnitude only, which has the advantage of improved SNR (Signal to Noise Ratio) over incoherent measurements, or coherent phase as well which can improve convergence times. Ultimately, due to the iterative use of the error signal as feedback 418, the scattering medium output wave 408 becomes optimized into a focused wave resulting from interaction with the scattering medium 406 and thus may be focused at a select location and area (as shown in FIG. 3) on the optical detector 416 and may have increased power or intensity at the select location. According to some example embodiments, the resulting wave may be focused on a single selected pixel of the optical detector.

Further, to determine if the shaped wave output from the spatial light modulator 403 has been optimized, the processing circuitry 420 may be configured to measure the intensity of the light being received at the select location (e.g., the focusing location) on the optical detector 416 and in a selected area at that location. The selected area size may be less than or the same as the transverse coherence length of the coherent optical receiver 401. According to some example embodiments, optimization may occur when the intensity has exceeded or increased by a threshold amount at the selected area at the selected location of the optical detector 416. Once the shaped wave 404 is optimized, the processing circuitry 420 may be configured to perform additional imaging analysis on the mixed wave 414 received by the optical detector 416 to extract additional information (e.g., phase, amplitude, frequency, or the like) or present a corrected image that eliminates the scattering effects of the scattering medium 406.

Figure 5:
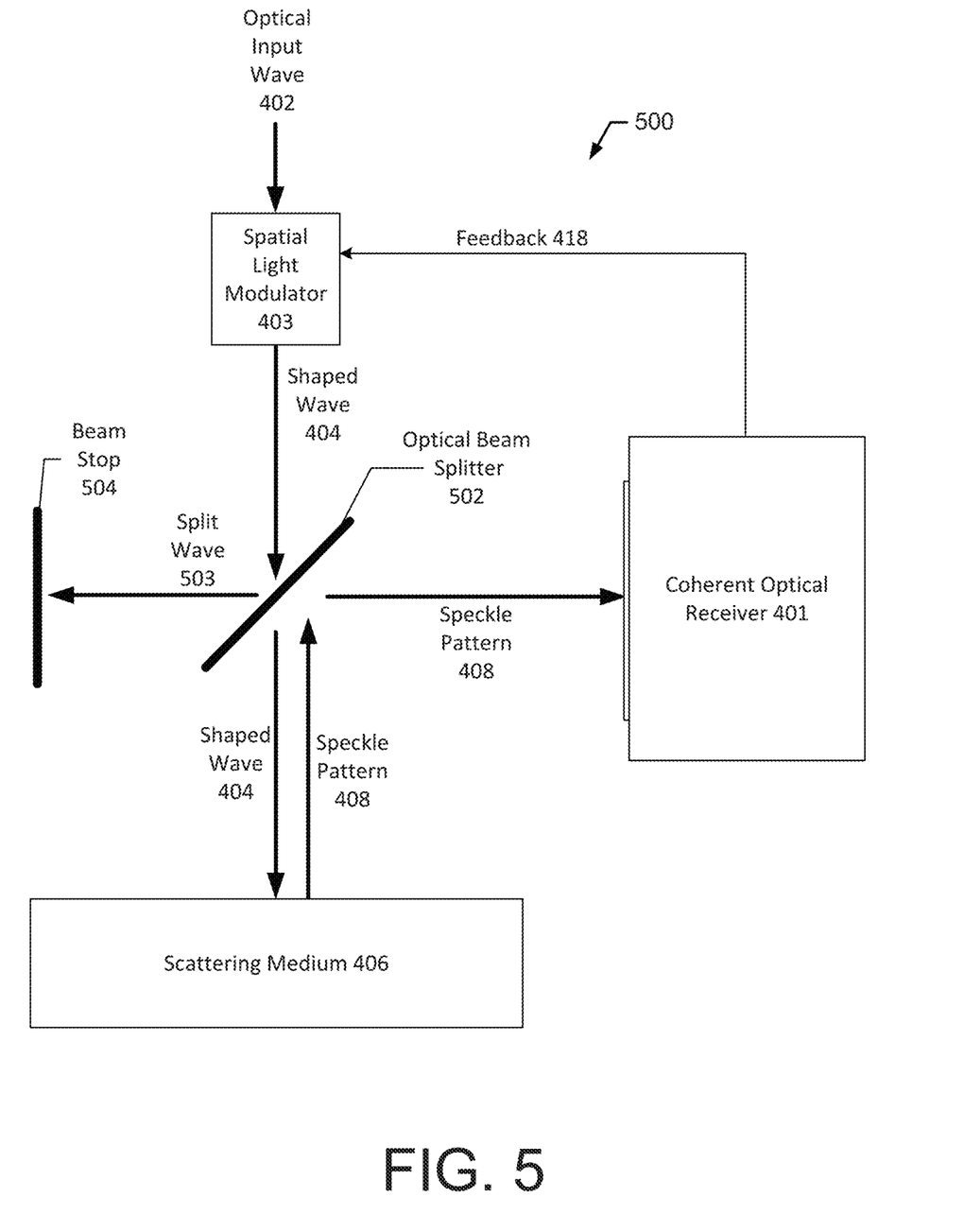
FIG. 5 illustrates a block diagram of an imaging system comprising a coherent optical receiver and a scattering medium in a reflective configuration according to various example embodiments.

FIG. 5 illustrates another block diagram of an imaging system 500 configured to operate in a reflection configuration relative to the scattering medium 406. The system 500 operates similar to the system 400, except that the scattering medium output wave 408 is formed as a reflected wave from the scattering medium 406. Similar to the above, the system 500 may comprise the coherent optical receiver 401 according to various example embodiments. The system 500 may also include the spatial light modulator 403. According to some example embodiments, as further described herein, via the spatial light modulator 403, an optical input wave 402 may be subjected to an iterative wavefront shaping process based on, for example, closed-loop feedback provided by the coherent optical receiver 401 as described above with respect to imaging system 400.

In the configuration shown in FIG. 5, the optical input wave 402 may be received by the spatial light modulator 403 and a shaped wave 404 may be output in same or similar manner as previously described. The shaped wave 404 may interact with the optical beam splitter 502, and a component of the shaped wave 404, i.e., split wave 503, may be output to the beam stop 504. The shaped wave 404, or a component thereof, may be passed to the scattering medium 406 for interaction in a reflective configuration. The reflected wave from the scattering medium 406 (i.e., the scattering medium output wave 408) may comprise of many optical modes that together form a speckle pattern that can be provided to the coherent optical receiver 401 via the optical beam splitter 502. The coherent optical receiver 401 may operate in the same or similar manner to the description above. In this regard, an error signal in the form of feedback 418 may be provided to the spatial light modulator 403 to support iterative improvement of the scattering medium output wave 408. Similar to the above, the shaped wave 404 may be considered optimized when the intensity at a select location on the optical detector 416 of the coherent optical receiver 401 reaches or increases by a threshold amount.

As indicated above, the use of the coherent optical receiver 401 realizes an ability to measure both amplitude and phase of a received wave at the optical detector 416 by performing mixing with the local oscillator wave 412 prior to detection. The coherent optical receiver 401 can offer improvements over, for example, incoherent approaches, through enhanced sensitivity. However, for a coherent optical receiver, such as coherent optical receiver 401, the detector area (e.g., dimensional size of the optical detector 416) may be limited by the transverse coherence length. In other words, the detector area or size may be limited to the size of a single speckle grain within the speckle pattern formed by the scattering medium 406.

In this regard, in a coherent optical receiver such as coherent optical receiver 401, the signal-to-noise ratio (SNR) may not improve after the detector size exceeds the size of a received speckle. When considering a single speckle, the phase of the received light can be relatively constant across the single speckle grain. As such, the signal strength may scale with the received signal power, or equivalently the detector area. However, optical shot noise can scale as the square root of the received power or detector area. Accordingly, the SNR increases with the area of the detector, but only within a single coherence area (or speckle).

With respect to an approach considering the analysis of multiple speckle grains, each speckle grain can have a different and random mean phase value. By summing, for example, N random phase sinusoids (associated with each respective speckle grains), a new signal having an amplitude equal to the square root of N can be realized. Stated differently, coherent signal amplitude will increase as the square root of detector area in this limit. As mentioned previously, the noise scales as the square root of area as well. As such, the SNR may not improve beyond the single speckle grain due to the equivalence of signal and noise scaling with the detector area making larger detectors inferior for this purpose.

Accordingly, to employ a coherent receiver design and realize the improved sensitivity of the design, achieving satisfactory SNR may be a challenge. To do so, as described herein, wavefront shaping has been leveraged. In this regard, the use of wavefront shaping can dramatically increase the SNR due to the ability to focus and concentrate the output wave from the scattering medium 406 at a select location of an optical detector, thereby allowing the power of the output wave from the scattering medium 406 to be concentrated within a single transverse coherence area, thereby facilitating the use of a small area optical detector and coherent detection.

Figure 6:
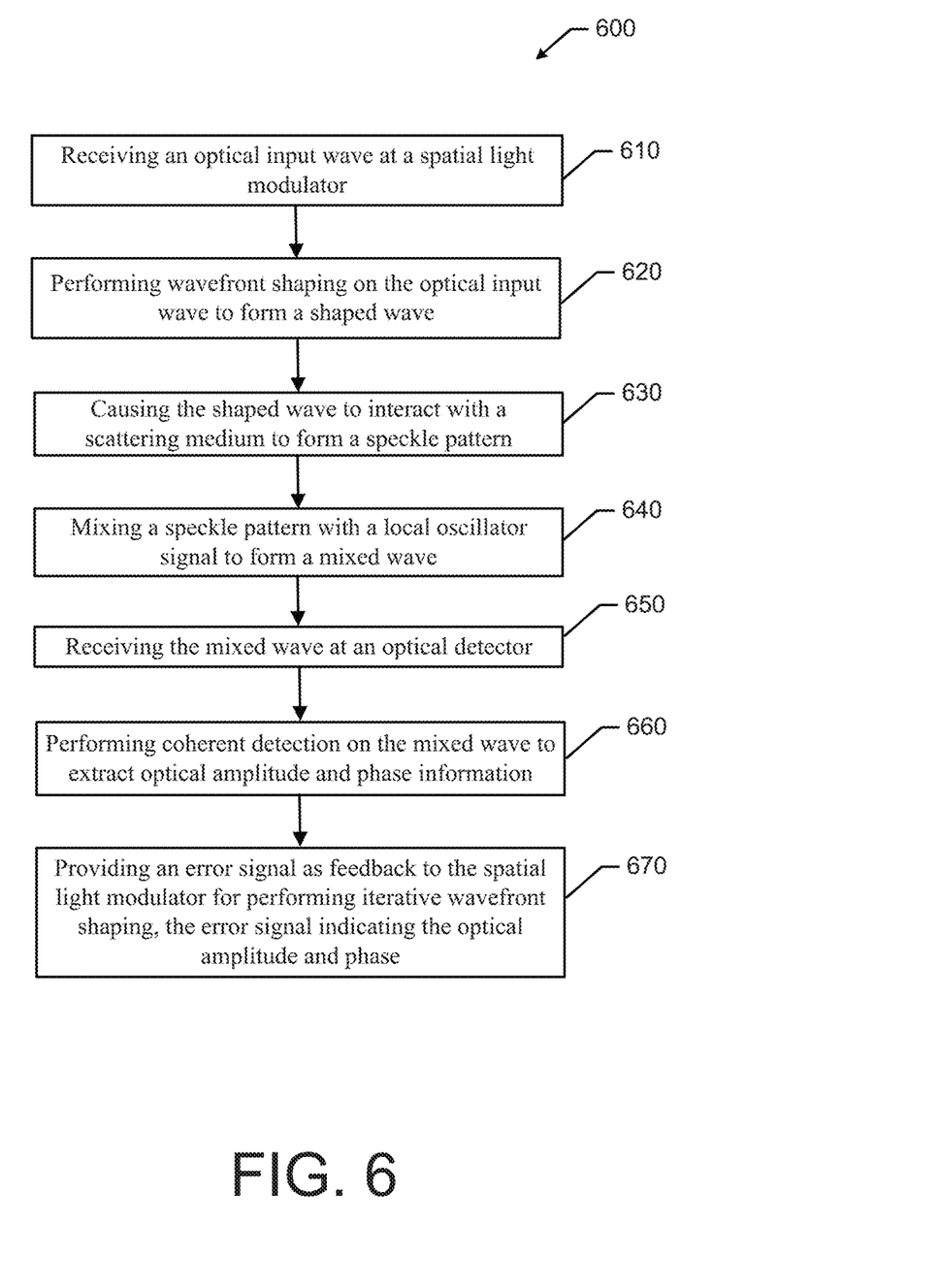
FIG. 6 shows an exemplary block diagram of a method for optical imaging according to various example embodiments.

FIG. 6 shows a flowchart 600 of an example method for optical imaging according to some example embodiments. The example method may include, at 610, receiving an optical input wave at a spatial light modulator, and, at 620, performing wavefront shaping, by the spatial light modulator, on the optical input wave to form a shaped wave. Further, at 630, the example method may include causing the shaped wave to interact with a scattering medium (e.g., in a transmission configuration or a reflective configuration) to form a speckle pattern. At 640, the example method may include mixing the speckle pattern with a local oscillator wave to form a mixed wave. At 650, the example method may include receiving the mixed wave at an optical detector. Further, at 660, the example method may include performing coherent detection on the mixed wave to extract optical amplitude and phase information. At 670, the example method may also include providing an error signal as feedback to the spatial light modulator for performing iterative wavefront shaping. In this regard, the error signal may indicate the optical amplitude and phase.

In some embodiments, additional optional operations may be included or the operations described above may be modified or augmented. Each of the additional operations, modification or augmentations may be practiced in combination with the operations above and/or in combination with each other. Thus, some, all or none of the additional operations, modification or augmentations may be utilized in some embodiments.

In this regard, according to some example embodiments, providing the error signal may include providing the error signal as feedback for iterative wavefront shaping to focus the resultant wave leaving the scattering medium and increase the intensity of the mixed wave on the optical detector by a threshold intensity at a select location. Additionally or alternatively, performing wavefront shaping may be based on speckle correlations of the speckle pattern. Additionally or alternatively, the local oscillator wave may be provided for heterodyne mixing or homodyne mixing when the speckle pattern is mixed with the local oscillator wave. Additionally or alternatively, the local oscillator wave may be provided in the form of a laser. Additionally or alternatively, the optical detector may be a pixelated camera or a monolithic optical detector, or the scattering medium may be biological tissue.

Some of the operations indicated in the flowchart 600 (e.g., performing coherent detection and providing an error signal) may be implemented by various means, such as hardware, firmware, processor, circuitry and/or other device associated with execution of software including one or more computer program instructions. For example, one or more of the procedures described above may be embodied by computer program instructions. In this regard, the computer program instructions which embody the procedures described above may be stored by a memory device executed by a processor of processing circuitry. As will be appreciated, any such computer program instructions may be loaded onto a computer or other programmable apparatus (e.g., hardware) to produce a machine, such that the instructions which execute on the computer or other programmable apparatus create means for implementing the functions specified in the flowchart block(s). These computer program instructions may also be stored in a computer-readable memory that may direct a computer or other programmable apparatus to function in a particular manner, such that the instructions stored in the computer-readable memory produce an article of manufacture which implements the functions specified in the flowchart block(s). The computer program instructions may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

The embodiments present herein are provided as examples and therefore the associated inventions are not to be limited to the specific embodiments disclosed. Modifications and other embodiments are intended to be included within the scope of the appended claims. Moreover, although the foregoing descriptions and the associated drawings describe example embodiments in the context of certain example combinations of elements and/or functions, different combinations of elements and/or functions may be used to form alternative embodiments. In this regard, for example, different combinations of elements and/or functions other than those explicitly described above are also contemplated. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments.

That which is claimed:

1. A system comprising:
   a spatial light modulator configured to receive an optical input wave and perform wavefront shaping on the optical input wave to output a shaped wave; and
   a coherent optical receiver comprising:
   an optical local oscillator configured to output a local oscillator wave at a local oscillator frequency;

an optical beam splitter configured to receive a scattering medium output wave and the local oscillator wave and mix the scattering medium output wave with the local oscillator wave to form a mixed wave, the scattering medium output wave being a resultant wave of the shaped wave interacting with a scattering medium and the scattering medium output wave at least initially comprising a speckle pattern;

an optical detector configured to receive the mixed wave and output an electrical signal representative of the mixed wave; and processing circuitry configured to:
receive the electrical signal from the optical detector;
perform coherent detection on the electrical signal to extract optical amplitude and phase information corresponding to the mixed wave; and
provide an error signal as feedback to the spatial light modulator for performing iterative wavefront shaping of the optical input wave, the error signal indicating the optical amplitude and phase information.

2. The system of claim 1, wherein the processing circuitry is configured to provide the error signal as feedback for iterative wavefront shaping to focus the scattering medium output wave and increase the intensity of the mixed wave on the optical detector by a threshold intensity at a select location on the optical detector.

3. The system of claim 1, wherein the spatial light modulator is configured to perform wavefront shaping based on speckle correlations between the optical input wave and the speckle pattern.

4. The system of claim 1, wherein the optical local oscillator is configured to output the local oscillator wave for heterodyne mixing or homodyne mixing with the scattering medium output wave by the optical beam splitter.

5. The system of claim 1, wherein the spatial light modulator is configured to perform iterative wavefront shaping based on a gradient ascent or genetic algorithm.

6. The system of claim 1, wherein optical detector comprises a pixelated camera or a monolithic optical detector.

7. The system of claim 1, wherein the scattering medium is biological tissue.

8. A method comprising:
receiving an optical input wave at a spatial light modulator;
performing wavefront shaping, by the spatial light modulator, on the optical input wave to form a shaped wave;
causing the shaped wave to interact with a scattering medium and output a scattering medium output wave at least initially comprising a speckle pattern;
mixing the scattering medium output wave with a local oscillator wave to form a mixed wave;
receiving the mixed wave at an optical detector;
performing coherent detection on the mixed wave to extract optical amplitude and phase information; and
providing an error signal as feedback to the spatial light modulator for performing iterative wavefront shaping on the optical input wave, the error signal indicating the optical amplitude and phase information.

9. The method of claim 8, wherein providing the error signal includes providing the error signal as feedback for iterative wavefront shaping to focus the scattering medium output wave and increase the intensity of the mixed wave on the optical detector by a threshold intensity at a select location.

10. The method of claim 8, wherein performing wavefront shaping is based on speckle correlations between the optical input wave and the speckle pattern.

11. The method of claim 8, wherein the local oscillator wave is for heterodyne mixing or homodyne mixing when the scattering medium output wave is mixed with the local oscillator wave.

12. The method of claim 8, wherein providing the error signal includes providing the error signal as feedback for iterative wavefront shaping based on a gradient ascent or genetic algorithm.

13. The method of claim 8, wherein the optical detector is a pixelated camera or monolithic optical detector.

14. The method of claim 8, wherein the scattering medium is biological tissue.

15. A coherent optical receiver in an imaging system comprising a spatial light modulator configured to receive an optical input wave and perform wavefront shaping on the optical input wave to output a shaped wave, the coherent optical receiver comprising:
an optical local oscillator configured to output a local oscillator wave at a local oscillator frequency;
an optical beam splitter configured to receive a scattering medium output wave and the local oscillator wave and mix the scattering medium output wave with the local oscillator wave to form a mixed wave, the scattering medium output wave being a resultant wave of a shaped wave interacting with a scattering medium and the scattering medium output wave at least initially comprising a speckle pattern;
an optical detector configured to receive the mixed wave and output an electrical signal representative of the mixed wave; and
processing circuitry configured to:
receive the electrical signal from the optical detector;
perform coherent detection on the electrical signal to extract optical amplitude and phase information; and
provide an error signal as feedback to the spatial light modulator for performing iterative wavefront shaping of the optical input wave, the error signal indicating the optical amplitude and phase information.

16. The coherent optical receiver of claim 15, wherein the processing circuitry is configured to provide the error signal as feedback for iterative wavefront shaping to focus the scattering medium output wave and increase the intensity of the mixed wave on the optical detector by a threshold intensity at a select location.

17. The coherent optical receiver of claim 15, wherein the optical local oscillator is configured to output the local oscillator wave for heterodyne mixing or homodyne mixing with the with the speckle pattern by the optical beam splitter.

18. The coherent optical receiver of claim 15, wherein the optical local oscillator is configured to provide the local oscillator wave in the form of a laser.

19. The coherent optical receiver of claim 15, wherein the optical detector comprises a pixelated camera or a monolithic optical detector.

20. The coherent optical receiver of claim 15, wherein the scattering medium is biological tissue.

* * * * *